United States Patent
Long

(12) 
(10) Patent No.: US 6,254,268 B1
(45) Date of Patent: Jul. 3, 2001

(54) BONE CEMENT MIXING APPARATUS

(75) Inventor: Jack F. Long, Warsaw, IN (US)

(73) Assignee: Depuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 09/354,634

(22) Filed: Jul. 16, 1999

(51) Int. Cl.[7] .................................................. B01F 13/06
(52) U.S. Cl. ........................................... 366/139; 366/247
(58) Field of Search .............................. 366/96–98, 130, 366/139, 241–248, 288, 605, 249–252

(56) References Cited

U.S. PATENT DOCUMENTS

| | | |
|---|---|---|
| 856,295 * | 6/1907 | Prindle . |
| 1,101,199 * | 6/1914 | Legg et al. . |
| 1,459,148 * | 6/1923 | Flynt . |
| 1,698,402 * | 1/1929 | Harris . |
| 2,150,888 * | 3/1939 | Barnard . |
| 2,269,736 | 1/1942 | Rogers . |
| 2,561,203 * | 7/1951 | Joffe . |
| 2,570,126 * | 12/1951 | Hobbs . |
| 2,696,022 * | 12/1954 | Steinbock et al. . |
| 2,898,094 * | 8/1959 | O'Neill, Jr. . |
| 3,053,457 | 9/1962 | Trumbull et al. . |
| 3,640,510 | 2/1972 | Lea . |
| 3,704,007 * | 11/1972 | Kroeger . |
| 4,079,917 | 3/1978 | Popeil . |
| 4,149,455 * | 4/1979 | Ross ..................................... 366/247 |
| 4,185,072 | 1/1980 | Puderbaugh et al. . |
| 4,460,279 * | 7/1984 | Krasney ................................ 366/247 |
| 4,488,817 * | 12/1984 | Uesaka et al. ........................ 366/247 |
| 4,671,263 | 6/1987 | Draenert . |
| 4,721,390 | 1/1988 | Lidgren . |
| 4,758,096 | 7/1988 | Gunnarsson . |
| 4,787,751 | 11/1988 | Bakels . |
| 4,854,716 | 8/1989 | Ziemann et al. . |
| 4,961,647 | 10/1990 | Coutts et al. . |
| 5,094,543 * | 3/1992 | Mursa ................................... 366/247 |
| 5,145,250 | 9/1992 | Planck et al. . |
| 5,199,788 * | 4/1993 | Stallings .............................. 366/605 |
| 5,252,301 | 10/1993 | Nilson et al. . |
| 5,265,956 | 11/1993 | Nelson et al. . |
| 5,328,262 | 7/1994 | Lidgren et al. . |
| 5,344,232 | 9/1994 | Nelson et al. . |
| 5,348,391 | 9/1994 | Murray . |
| 5,368,386 | 11/1994 | Murray . |
| 5,374,121 | 12/1994 | Draenert . |
| 5,395,167 | 3/1995 | Murray . |
| 5,415,474 | 5/1995 | Nelson et al. . |
| 5,435,645 * | 7/1995 | Faccioli et al. . |
| 5,472,445 | 12/1995 | Yakimicki et al. . |
| 5,494,349 | 2/1996 | Seddon . |
| 5,501,520 | 3/1996 | Lidgren et al. . |
| 5,505,538 | 4/1996 | Earle . |
| 5,549,381 | 8/1996 | Hays et al. . |
| 5,551,778 | 9/1996 | Hauke et al. . |

(List continued on next page.)

FOREIGN PATENT DOCUMENTS

| | | |
|---|---|---|
| 0 616 552 B1 | 9/1994 | (EP) . |
| 86 06781 | 4/1986 | (FR) . |
| 178572 | 4/1922 | (GB) . |
| 517340 | 1/1940 | (GB) . |
| WO 88/08327 | 11/1988 | (WO) . |
| WO 93/10892 | 6/1993 | (WO) . |
| WO 99/06140 | 2/1999 | (WO) . |

*Primary Examiner*—Charles E. Cooley
(74) *Attorney, Agent, or Firm*—Maginot, Addison & Moore

(57) ABSTRACT

The present invention relates to a bone cement mixing apparatus for mixing a quantity of monomer from a monomer dispensing apparatus with a quantity of bone cement in the presence of a vacuum. The mixing device includes a bowl, a lid connectable to the bowl, a luer lock connectable with a luer from the monomer dispensing apparatus, a crank rotatably connectable to the lid and extending through the lid, a blade off-set positioned inside the bowl and non-concentrically connected to the crank, and a vacuum source connectable to the device.

14 Claims, 5 Drawing Sheets

U.S. PATENT DOCUMENTS

| | | |
|---|---|---|
| 5,558,136 | 9/1996 | Orrico . |
| 5,571,282 | 11/1996 | Earle . |
| 5,624,184 | 4/1997 | Chan . |
| 5,797,678 * | 8/1998 | Murray ................................. 366/139 |
| 5,797,679 * | 8/1998 | Grulke et al. ........................ 366/244 |
| 5,961,211 * | 10/1999 | Barker et al. ........................ 366/139 |

* cited by examiner

BONE CEMENT MIXING APPARATUS

BACKGROUND AND SUMMARY OF THE INVENTION

The present invention relates to bone cement mixing apparatuses. More particularly, the present invention relates to a bone cement mixing apparatus for mixing bone cement in the presence of a vacuum.

It is necessary in many orthopedic surgical procedures to employ a cement or grouting type agent, such as for attaching artificial joint implants, repairing or forming joints in bones, or other forms of orthopedic work. The type of cement generally used for these purposes are self-curing resins formed from the blending of a wide variety of liquid monomers or comonomers with powdered polymers or copolymers to form a viscous admixture to be used as the grouting agent. The admixture of the powder and liquid components develops a quick setting material and preparation of the cement usually occurs directly within the operating theater just prior to use.

It is known to add a monomer to dry bone cement via a monomer delivery apparatus. See for example, U.S. patent application Ser. No. 09/293,396, filed Apr. 16, 1999, entitled Monomer Delivery Device for Bone Cement Delivery System, the disclosure of which is hereby incorporated by reference. In such an apparatus, the monomer agent and the bone cement are mixed in the presence of a vacuum. The mixture being subjected to the vacuum serves a dual role. First, the vacuum serves to evacuate fumes the monomer used in the mixture may produce. Second, the vacuum actively reduces the amount of air bubbles or vapor pockets in the mixture during the mixing process.

According to the present invention bone cement mixing apparatus is provided that comprises a bowl, a lid that is removably attached to the bowl, a crank extending through and removably attached to the lid, and a blade positioned in the bowl. The lid includes a sealable monomer delivery port. In addition, the blade is attached to the crank such that the blade rotates with the crank. In preferred embodiments, the blade is non-concentrically shaped and has a vane attached thereon to increase the mixing and shearing action.

In a further embodiment of the present invention, a vacuum outlet may be attached to either the lid, handle, or bowl. The outlet attaches to a vacuum hose that routes air and vapors away from the mixing bowl. In a still further embodiment, the mixing bowl includes a plurality of intermittent shims placed about the circumference of the bowl so that the outer edge of the lid having several annular intermittent flanges cooperate with each intermittent shim on the bowl. In an additional embodiment, the mixing blade contours about one quarter the circumference of the bowl. The blade may also include an angled shoulder blade.

Additional features of the present invention will become apparent to those skilled in the art upon consideration of the following detailed description of preferred embodiments exemplifying the best mode of carrying out the invention as presently perceived.

DETAILED DESCRIPTION OF THE INVENTION

Figures 1, 2:
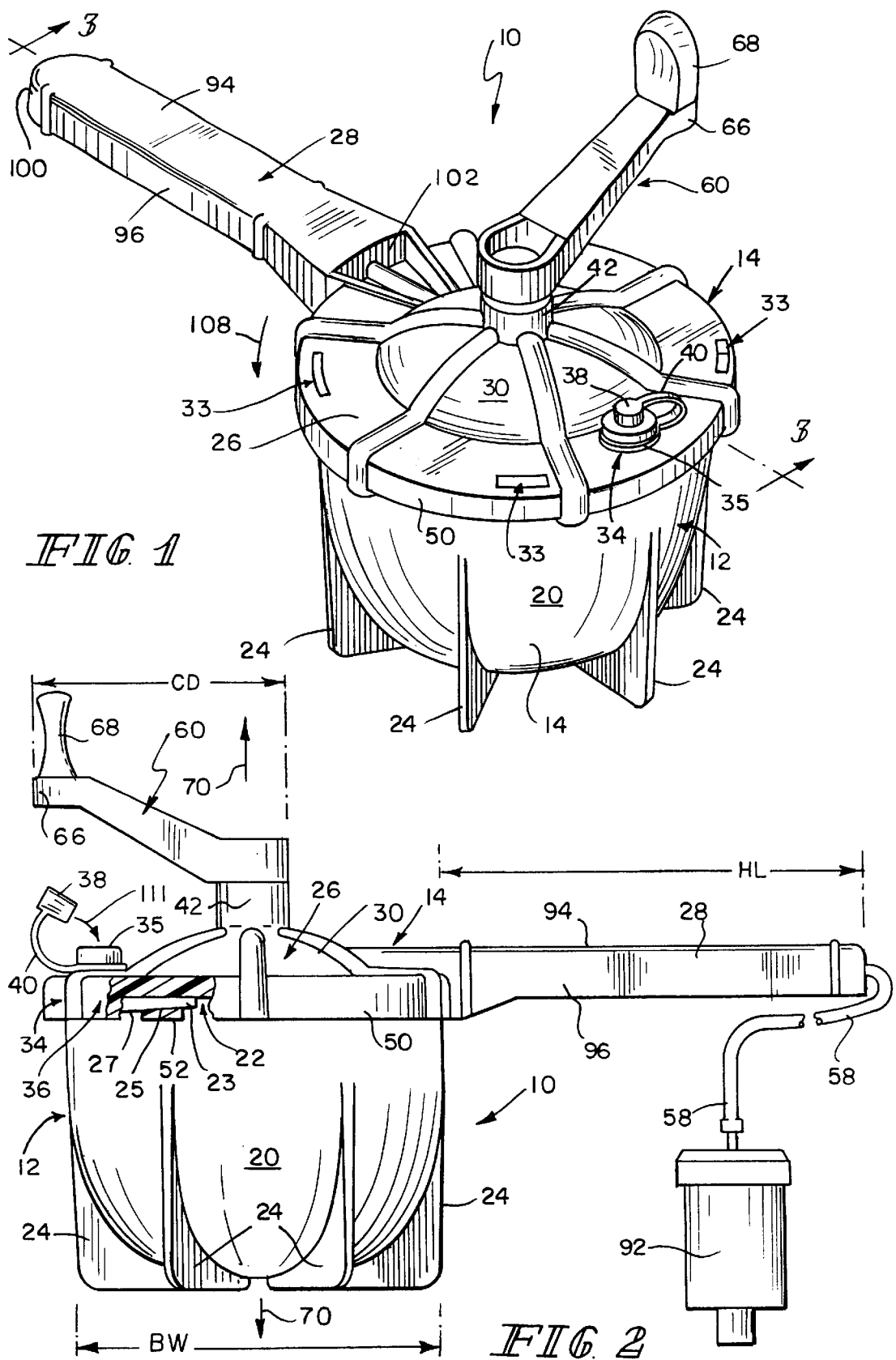
FIG. 1 is a perspective view of bone cement mixing apparatus in accordance with the present invention, showing the apparatus including a bowl, a lid including a luer lock having a body and a cap, and a crank.
FIG. 2 is a right-side elevation view of the apparatus of FIG. 1, showing the body of the luer lock defining a delivery port, the cap removed from the body, the lid coupled to the bowl by intermittent flanges on the lid fitted under corresponding shims on the bowl, a vacuum tube extending from the lid, and a vacuum pump.

A bone cement mixing apparatus 10 is provided in accordance with the present invention. Mixing apparatus 10 is configured to receive a quantity of bone cement and monomer and mix the cement and monomer under a vacuum. The mixture may then be removed and applied in a prosthesis or deposited in a cement delivery device. As shown in FIGS. 1 and 2, mixing apparatus 10 comprises a bowl 12 and a lid 14 coupled to bowl 12.

Figure 3:
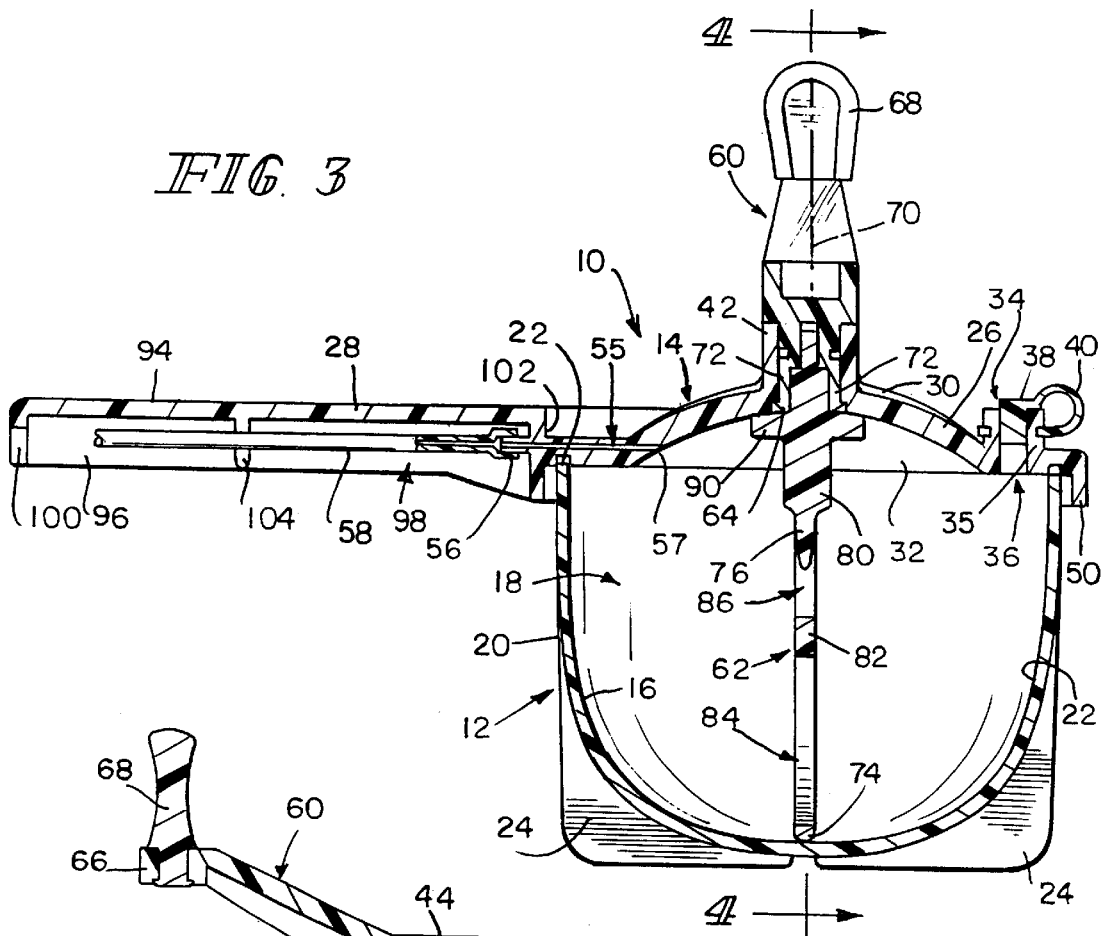
FIG. 3 is a view along lines 3—3 of FIG. 1, showing the cap situated in the delivery port of the body to form a seal between the body and cap and a blade rotatably coupled to the lid.
Figure 4:
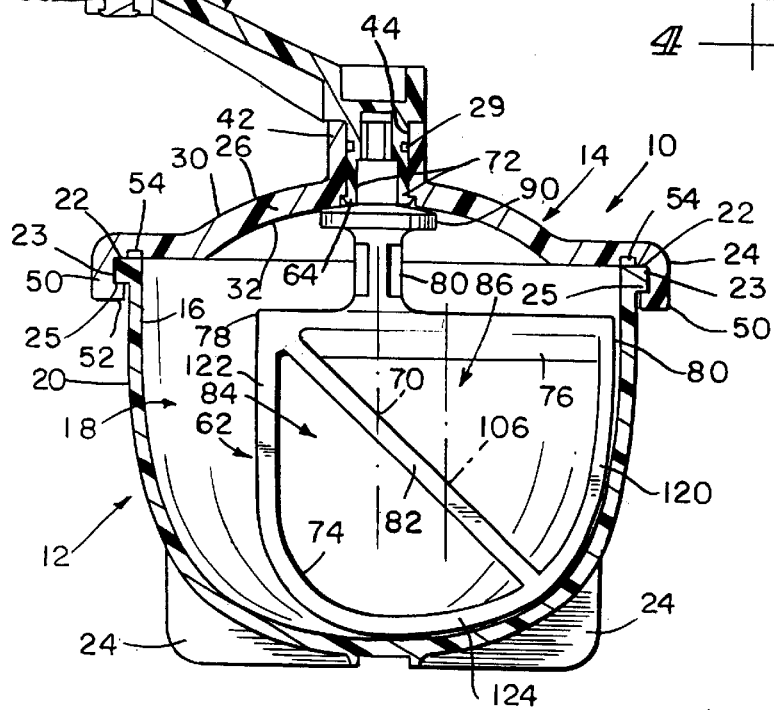
FIG. 4 is a view along lines 4—4 of FIG. 3, showing the crank sealing coupled to the lid and the blade coupled to the crank and including a vane.

Referring now to FIG. 3, bowl 12 includes an inner surface 16 that defines a cavity 18, an outer surface 20, and an upper rim 22 extending between inner and outer surfaces 16, 18. As shown in FIGS. 2–4, shims 23 extend intermittently about rim 22 of bowl 12. In this embodiment, each shim 23 has a slight depending slope 27 (FIG. 2) formed at a bottom surface 25 so that as lid 14 engages bottom surface 25, the slope forces lid 14 to make a tighter fit against rim 18. In addition, outer surface 20 is formed to include leg flanges 24 that serve as a stable base.

As shown in FIGS. 1–4, lid 14 covers bowl 12, being sealably and removably attachable so that air does not escape between lid 14 and bowl 12. Lid 14, however, is removable so that dry bone cement can be placed into cavity 18 of bowl 12, and the wet bone cement can be removed from cavity 18 after the dry bone cement is mixed with a monomer. Lid 14 comprises a cover 26 and a handle 28 extending from cover 26. The bowl 12 possesses a bowl width BW, and the handle 28 possesses a handle length HL. As shown in FIG. 2, the handle length HL is greater than the bowl width BW.

Cover 26 includes an outer surface 30 and an inner surface 32 facing inner surface 16 of bowl 12. As shown in FIG. 2, a ridge 50 extends about an outer perimeter of cover 26. In addition, several intermittent annular flanges 52 extend radially inward from ridge 50. Thus, when lid 14 is placed over rim 18 of bowl 12 and is rotated, each intermittent flange 52 contacts bottom surface 25 of corresponding shim 23. In addition, slots 33 extend through cover 26 in general alignment with a gasket 54, which extends across slots 33 to prevent air and vapors from leaking therethrough. Gasket 54 is positioned between lid 14 and rim 18, assisting in creating a seal between the two components. It is appreciated, however, that a variety of attachment means can be used to sealably and removably attach lid 4 onto bowl 12. For example, an annular snap fit or threads may be used in place of the annular flange/shim structures. In addition, as shown in FIG. 3, cover is formed to include a vacuum passageway 55 extending therethrough. Vacuum passageway 55, as shown in FIG. 1, includes a vacuum inlet 57 formed through inner surface 32 of cover 26 and a vacuum outlet 56 positioned to lie adjacent to handle 28.

Cover 26 also includes a luer lock 34 and a crank mount 42 extending from outer surface 30 and defining a shaftway 44. Luer lock 34 includes a body 35 that defines a delivery port 36 extending between inner and outer surfaces 32, 30. In addition, luer lock 34 includes a cap 38 that is sized for extension into delivery port 36 and that removably seals body 35 and a tether 40 extending between cap 38 and body 35. Luer lock 34 is configured such that a luer or spout from a monomer dispensing device (not shown) may be extended through delivery port 36 forming a sealing fit with body 35. Thus luer lock 34 allows monomer to be dispensed into bowl 12 while preventing monomer vapors from escaping between the luer (not shown) and luer lock 34.

Cap 38 is used to seal body 35 after the monomer has been dispensed into bowl 12 and during the mixing process. Cap 38 is shown in a disengaged position in FIG. 2. Cap 38 is removed from body 35 in anticipation for the luer attached to the monomer dispensing device (not shown) being inserted for the purpose of transferring monomer from the dispensing device into mixing bowl 2. It will be appreciated that a variety of luer locks and luer lock caps may be used in place of luer lock 34. For example, a self-closing luer lock may be used eliminating even the need for luer cap 38 or a threaded luer lock may be used to screw cap 38 onto body 35. In another embodiment, the monomer dispensing device (not shown) itself may be used as a seal for the luer lock.

Figure 6:
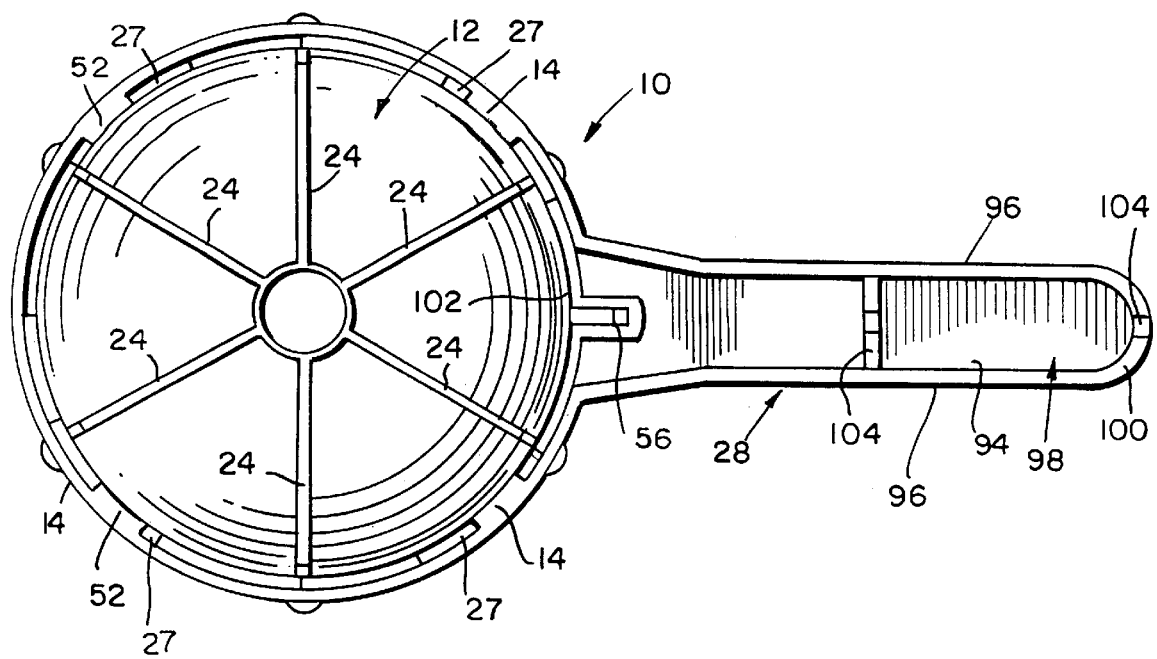
FIG. 6 is a bottom view of the apparatus of FIG. 1 showing the bowl including leg flanges, the lid including a handle having a vacuum outlet and hose grips spaced-apart from the vacuum outlet.

Handle 28 of lid 14 extends from cover 26. In one embodiment, handle 28 serves a dual function. First, as a grippable body for an operator to hold while mixing the bone cement, and second, to provide a conduit for vacuum outlet 56 (see FIGS. 3 and 6) and a vacuum tube 58 (see FIG. 2). It is appreciated, however, that handle 28 may be placed anywhere on mixing apparatus 10. For example, handle 28, in another illustrative embodiment may be attached to bowl 12 (not shown). In addition, vacuum outlet 56 may be disposed through bowl 12. Handle 28 includes a top wall 94, side walls 96, and opposite end walls 100, 102 that cooperate to define a cavity 98 therebetween. In addition, at least one tube grip 104 extends from top wall 94 into cavity 98.

Referring to FIGS. 3 and 4, mixing apparatus 10 includes a crank 60 co-rotatably coupled to lid 14. The crank 60 extends a distance CD in a horizontal direction as shown in FIG. 2. And the handle length HL is greater than the crank distance CD as further shown in FIG. 2. Crank 60 is used by the operator to drive a blade 62 off-set positioned inside bowl 12 and non-concentrically connected to crank 60 to mix the monomer and bone cement together. One end 64 of crank 60 is rotatably extended through shaftway 44, generally at the center of cover 26, while the other end 66 of crank 60 is attached to a knob 68. Crank 60 further includes legs 72 that are sized for rotation in shaftway 44 and are coupled to blade 62. Ultimately, end 64 of crank 60 is coupled to blade 62. Crank 60 is configured to rotate about a longitudinal axis 70 of shaftway 44 which is illustratively the same as the axis of rotation of cover 26. (See FIGS. 3 and 4.) Knob 68 is configured to serve as a grip which the operator may grasp to rotate crank 60 thereby causing blade 62 to rotate. It is appreciated that knob 68 may also be configured to rotatably or fixedly attach to crank 60. In addition, a small o-ring 29 is fitted between legs 72 and crank mount 42 in shaftway 44 to prevent the escape of air or vapor between lid 14 and crank 60.

Figure 5:
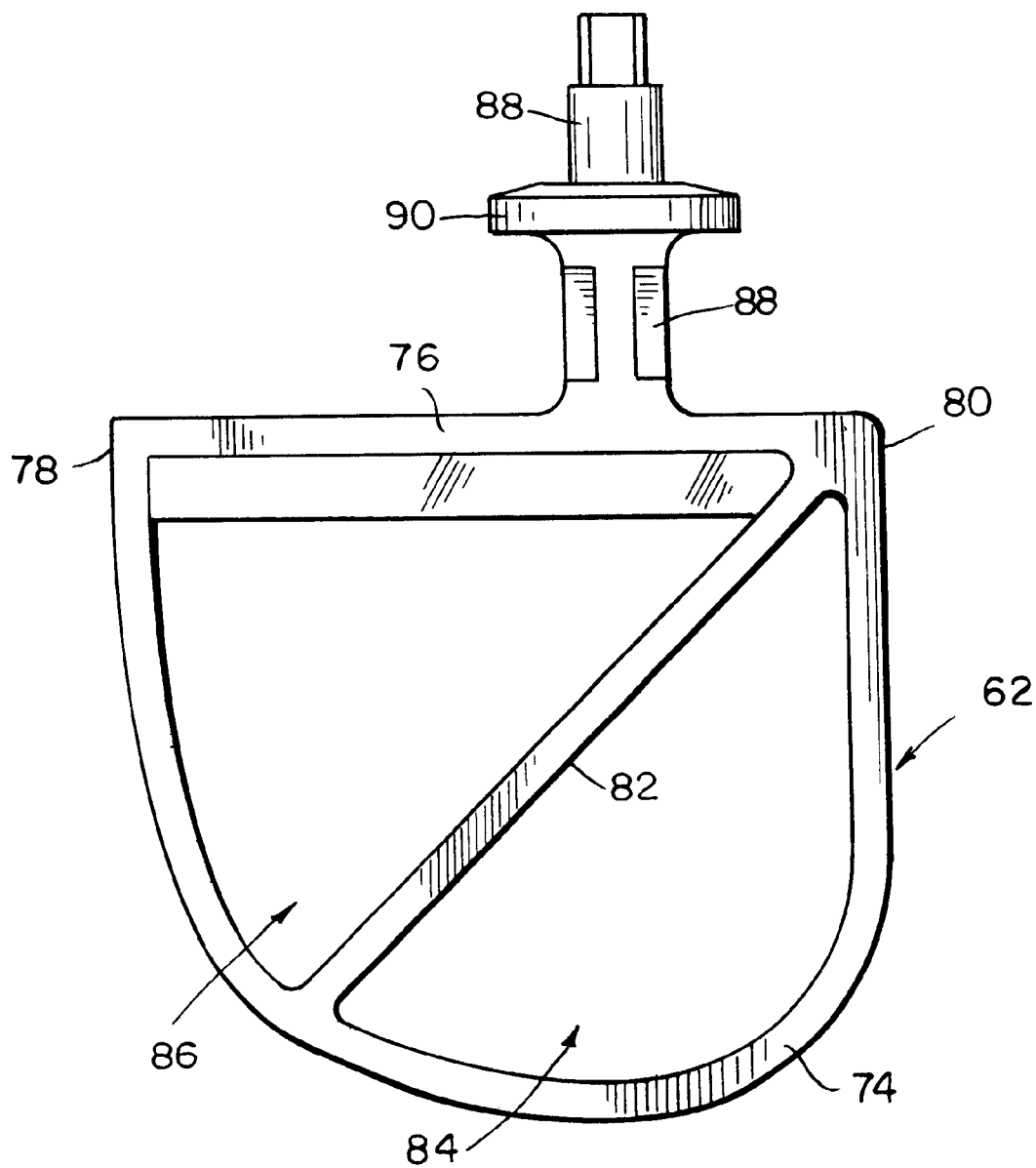
FIG. 5 is a front elevation view of the blade of FIG. 4 showing the blade including a generally U-shaped body, a shoulder blade extending across opposite ends of the body, the vane, a shaft extending from the shoulder blade, and a collar coupled to the shaft.

Rotation of legs 72 of crank 60 rotates blade 62 about longitudinal axis 70 of shaftway 44. As shown in FIGS. 4 and 5, blade 62 includes a generally U-shaped body 74 that has a non-symmetrical extended curved side 120, a generally linear side 122 opposite curved side 120, and a rounded bottom 124 connecting to sides 120, 122, Sides 120, 122 cooperate to define opposite ends 78, 80 of U-shaped body 74. In addition, blade 62 includes a plane top or shoulder blade 76 extending between and connecting opposite ends 78, 80 of body 74 and a vane 82 extending from one of the ends 78 of body 74 to rounded bottom 124 to define a first aperture 84 and a second aperture 86 and to shear and mix the cement nearer the center of bowl 12. In addition, blade 62 includes a shaft 88 that extends from shoulder blade 76 and a collar 90 coupled to shaft 88.

Shaft 88 extends upward from shoulder blade 76 into shaftway 44 and frictionally coupled to depending legs 72. It is understood, however, that the present invention is not limited to only a frictional fit between shaft 88 and crank 60. Any variety of means may connect blade 62 to crank 60, and are contemplated by the present invention. For example, a snap-fit or connectable threads may accomplish the same function. Collar 90 is configured to limit the length with which shaft 88 may extend through shaftway 44. Thus collar engages inner surface 32 of cover 26 to ensure proper placement of blade 62 in cavity 18 of bowl 12. Shaft 88 is also laterally offset from the longitudinal center 106 of blade 62. This offset placement creates additional shearing action per revolution of crank 60. The additional shearing action reduces the amount of mixing required to produce the wet cement.

Because crank 60 rotatably extends through shaftway 44 attaching itself to blade 62, blade 62 rotates as crank 60 is rotated by the operator thereby mixing the monomer with the cement inside bowl 12. Referring now to FIG. 4, for optimum mixing, at least a portion of blade 62 passes in close proximity to inner wall 22 of bowl 12 as well as being offset relative to shaft 20. In one embodiment, at least a portion of blade 62 contours about one quarter the circumference of bowl 12 and along a plane generally parallel to longitudinal axis 70 of shaftway 44.

Referring now to FIG. 3, vacuum tube 58 is coupled to vacuum outlet 56. In one illustrative embodiment vacuum tube 58 extends through end wall 102 and into cavity 98 of handle 28 so as not to interfere with the operator as apparatus 10 is being used. Vacuum tube 58 is also connectable to a vacuum pump 92 (FIG. 2) designed to draw air from mixing apparatus 10 through vacuum outlet 56. Vacuum tube 58 is illustratively secured into place by tube grips 104, which aid in ensuring that vacuum tube 58 remains coupled to vacuum outlet 56.

Figure 7:
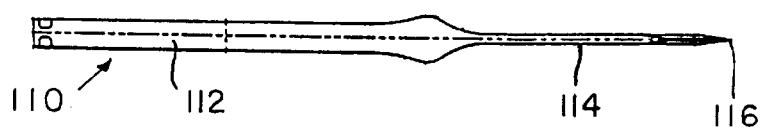
FIG. 7 is a top view of a spatula suitable for use with the apparatus of FIG. 1, showing the spatula including a handle and a blade formed for removing wet bone cement mixture from the bowl.
Figure 8:
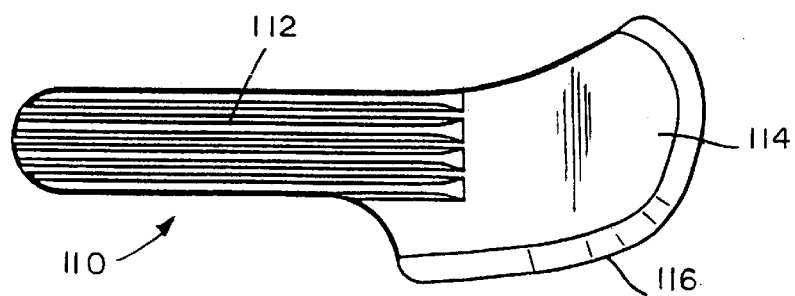
FIG. 8 is a side view of the spatula of FIG. 7.
Figure 9:
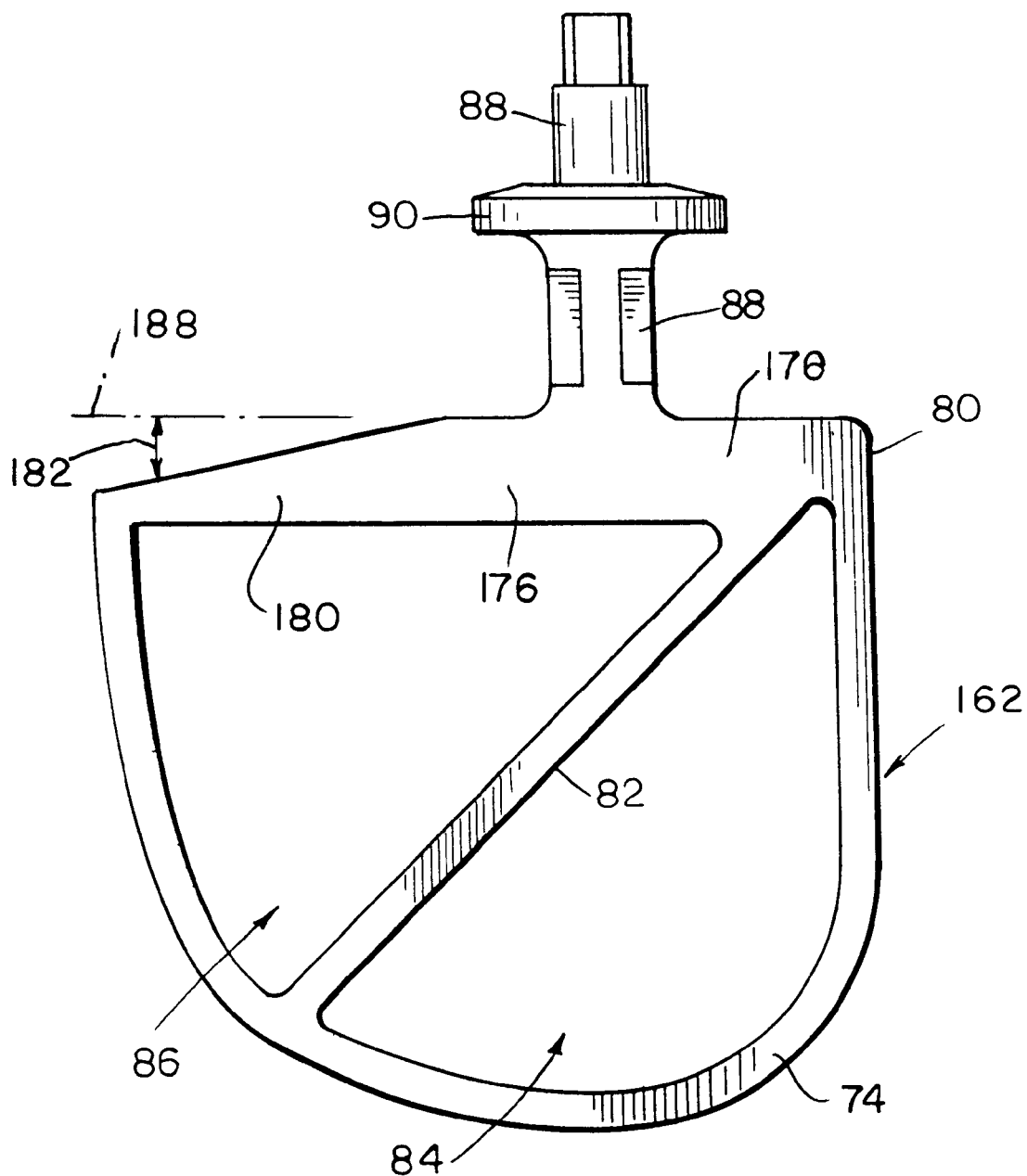
FIG. 9 is a front elevation view of an alternative blade suitable for use with the bowl and lid of FIG. 1, showing the blade including a generally U-shaped body, a tapered shoulder blade extending across opposite ends of the body, a vane extending from the shoulder blade, and a collar coupled to the shaft.

After the monomer and the bone cement are mixed together in mixing apparatus 10, lid 14 is rotated in an opposite direction 108 (FIG. 1) thereby releasing flanges 52 from shims 23 allowing removal of lid 14 from bowl 12. A spatula 110, as shown in FIGS. 7 and 8, may be used to remove the cement mixture from bowl 12. Spatula 110 includes a handle 112 and a blade 114 coupled to handle 112. Blade 114 is formed to have a curved outer edge 116 that is formed in the partial shape of the contour of inner wall 22. Handle 112 may be gripped by the operator to scoop out the wet cement from cavity 18, using blade 112, for deposit in a cement dispensing device (not shown) or directly onto a prosthetic setting (not shown).

In a further embodiment, blade 162 is provided in accordance with the present invention to be used in place of blade 62. Blade 162 is formed similarly to blade 62 and like reference numerals will be used to denote like components. Blade 162 is formed to include an angled shoulder blade 176. Illustratively, shoulder blade 176 includes a first portion 178 and a second tapered portion 180 that forms an angle generally obtuse from shaft 88. In one illustrative embodiment, the angle of shoulder blade identified by reference number 182 is about −15° relative to horizontal line 188. It is appreciated, however, that the angle of tapered portion 180 may be anywhere above or below horizontal line 188.

For method of manufacture of the wet bone cement mixture, a quantity of bone cement powder is placed in cavity 18 of bowl 12. As shown in FIG. 1, lid 14 is placed over rim 22 and rotated until each flange 52 contacts bottom surface 25 of corresponding shim 23 to press seal 54 against rim 18 and form a seal therebetween. Once lid 14 is sealably attached to bowl 12, monomer may added to the bone cement powder. To prevent the escape of vapors, it is preferable that the monomer be deposited after the cement has already been placed in bowl 12 and lid 14 is coupled to rim 18.

To place monomer in cavity 18, cap 38 is removed from body 35 of luer lock 34. Thereafter, vacuum pump 14 is activated generating a vacuum within bowl 12 to expel air from cavity 18 out through vacuum outlet 56 and tube 58. It is preferable to generate a vacuum in cavity 18 of about 0.67 to 0.73 bar, just below the boiling point of the monomer creating the maximum vacuum pressure in bowl 12 without the monomer boiling. Illustratively, once the vacuum has begun evacuating the air from cavity 18, the luer or similar structure from the monomer dispensing device (not shown) is inserted into delivery port 36 of body 35 to form a generally sealed connection at which time the monomer may be deposited into bowl 12. The vacuum pump 92 will expel from apparatus 10 any monomer vapors generated by the deposition of the monomer in bowl 12. After the monomer is deposited into bowl 12, the luer from the monomer delivery device (not shown) is removed from luer lock 34 and luer cap 38 is immediately fitted into delivery port 36, as shown by arrow 111 in FIG. 2.

After the monomer delivery device (not shown) is removed from mixing 10 apparatus 10, the operator grips handle 28 with one hand and gripping knob 68 on crank 60 with the other hand. The operator rotates crank 60 about longitudinal axis 70 of shaftway 44. Crank 60 causes body 74 and vane 82 of blade 62 to begin rotating within bowl 12 shearing and mixing the bone cement with the monomer, as previously discussed. An illustrative stirring time for efficient stirring of the mixture is about 45 to 60 seconds. It is preferable that the vacuum remains evacuating vapors from the mixture for about an additional 15 to 20 seconds after mixing has been completed to remove any excess air or monomer vapor from the bone cement mixture. Lid 14 is then rotated on bowl in direction 108 as previously discussed. The operator may then use spatula 110 to scrape the wet bone cement out from bowl 12. The wet bone cement can then be placed into a bone cement dispensing device (not shown) to then be applied to a prosthesis.

Although the invention has been described in detail with reference to a preferred embodiment, variations and modifications exist within the scope and spirit of the invention as described and defined in the following claims.

What is claimed is:

1. A bone cement mixing apparatus comprising:
   a bowl;
   a lid removably attached to the bowl having a sealable monomer delivery port disposed therethrough;
   a crank having a portion extending through the lid, said crank being rotatably attached to the lid; and
   a blade positioned in the bowl and attached to that portion of the crank extended through the lid such that the blade rotates with the crank.
   wherein (i) the lid also comprises a handle, and (ii) the handle comprises a vacuum outlet tube and tube grips for attachment to a vacuum source and vacuum tube.

2. The apparatus of claim 1, wherein the bowl further comprises a plurality of intermittent shims placed about the circumference of the bowl and the lid shrouds the bowl and has a plurality of annular intermittent flanges formed about the edge of the lid, whereby each flange cooperates with an intermittent shim on the bowl removably and sealably attaching the lid to the bowl.

3. The apparatus of claim 2, wherein the blade further comprises a vane fitted within the blade.

4. The apparatus of claim 1, further comprising a portion of the blade contouring about one quarter the circumference of the bowl along a plane parallel to the longitudinal axis of the blade.

5. The apparatus of claim 4, wherein the blade further comprises an angled shoulder blade.

6. The apparatus of claim 1, wherein the sealable port also comprises a luer port cap that selectively seals the port.

7. The apparatus of claim 1, wherein the blade is a U-shaped blade having a non-symmetrical extended curved side, a linear side opposite the curved side, a rounded bottom connecting to the linear side and the curved side, a plane top laterally extending also connecting to the linear side and the curved side, a vane extending from the plane top to the rounded bottom, and a shaft extending from the plane top.

8. The apparatus of claim 7, wherein the plane top comprises an angled shoulder blade.

9. The apparatus of claim 7, wherein the shaft is extending from a non-symmetrical position on the plane top.

10. The apparatus of claim 1, wherein the blade is positioned in the bowl and attached to that portion of the crank extended through the lid such that the blade rotates non-concentrically with the crank.

11. A bone cement mixing apparatus comprising:
    a bowl,
    a lid removably coupled to the bowl, the lid including a cover formed to include a delivery port therethrough and a cap formed for extension into the delivery port to selectively seal the port,
    a crank extending through and rotatably coupled to the lid, and
    a blade positioned in the bowl and coupled to the crank so that the blade rotates with the crank,
    wherein (i) the lid includes a handle extending outwardly from the cover, and (ii) the lid is formed to include a vacuum passageway extending between the cover and the handle.

12. The apparatus of claim 11, wherein the blade is formed to include a body portion and a shoulder blade extending between opposite ends of the body portion.

13. The apparatus of claim 12, wherein the shoulder blade includes a tapered portion.

14. The apparatus of claim 12, wherein the blade is formed to include a vane extending across the body portion.

* * * * *